(12) United States Patent
Hanawa et al.

(10) Patent No.: US 9,301,817 B2
(45) Date of Patent: Apr. 5, 2016

(54) DENTAL PROSTHESIS COMPONENT AND METHOD FOR PRODUCING DENTAL PROSTHESIS COMPONENT

(71) Applicants: TOKYO MEDICAL AND DENTAL UNIVERSITY, Tokyo (JP); GC CORPORATION, Tokyo (JP)

(72) Inventors: Takao Hanawa, Tokyo (JP); Shohei Kasugai, Tokyo (JP)

(73) Assignees: TOKYO MEDICAL AND DENTAL UNIVERSITY, Tokyo (JP); GC CORPORATION, Tokyo (JP)

( * ) Notice: Subject to any disclaimer, the term of this patent is extended or adjusted under 35 U.S.C. 154(b) by 48 days.

(21) Appl. No.: 14/035,123

(22) Filed: Sep. 24, 2013

(65) Prior Publication Data

US 2014/0147813 A1 May 29, 2014

(30) Foreign Application Priority Data

Nov. 27, 2012 (JP) .................................. 2012-258775

(51) Int. Cl.
*A61C 8/00* (2006.01)
*A61C 13/00* (2006.01)

(52) U.S. Cl.
CPC ............. *A61C 8/0015* (2013.01); *A61C 8/0069* (2013.01); *A61C 13/0006* (2013.01)

(58) Field of Classification Search
CPC .. A61C 8/0012; A61C 8/0013; A61C 8/0069; A61C 8/0015; A61K 6/04
See application file for complete search history.

(56) References Cited

U.S. PATENT DOCUMENTS

| | | | | |
|---|---|---|---|---|
| 5,372,660 A | * | 12/1994 | Davidson et al. | 148/421 |
| 5,415,704 A | * | 5/1995 | Davidson | 148/316 |
| 7,968,209 B2 | * | 6/2011 | Pawar et al. | 428/632 |
| 8,361,381 B2 | * | 1/2013 | Heuer et al. | 419/8 |

FOREIGN PATENT DOCUMENTS

JP         2010-046153         4/2010

* cited by examiner

*Primary Examiner* — Ralph Lewis
(74) *Attorney, Agent, or Firm* — Ladas & Parry LLP

(57) ABSTRACT

A dental prosthesis component which is a member for configuring a dental prosthesis provided with an artificial tooth root, which has a high strength and a good esthetic property. The dental prosthesis component which is a member for configuring a dental prosthesis provided with an artificial tooth root wherein the dental component is made of Zr-14Nb alloy, a surface layer containing $ZrO_2$ as a main constituent and having a thickness of 20 μm or more and less than 80 μm is formed on the dental prosthesis component, and the surface has a brightness of Gy 8.0 or more of the color sheets according to Practical Color Co-ordinate System 201.

4 Claims, 7 Drawing Sheets

600°C 10h (No.2)

700°C 0.5h (No.3)

700°C 10h (No.4)

800°C 0.5h (No.5)

800°C 1.0h (No.6)

800°C 2.0h (No.7)

900°C 0.5h (No.12)

900°C 1.0h (No.12)

DENTAL PROSTHESIS COMPONENT AND METHOD FOR PRODUCING DENTAL PROSTHESIS COMPONENT

TECHNICAL FIELD

The present invention relates to a dental prosthesis component which is a member for configuring a dental prosthesis such as an artificial tooth root (implant, fixture) or an abutment to be used for a dental prosthesis to repair defective sites in a tooth row by the artificial tooth root, and a method for producing the dental prosthesis component.

BACKGROUND ART

A dental prosthesis provided with an artificial tooth root includes: an artificial tooth root whose one end is to be embedded in a jawbone; an abutment to be disposed in a manner that one end thereof is fixated to the artificial tooth root and the other end projects into an oral cavity; and an artificial tooth crown disposed in a manner to cap the other end of the abutment projected into the oral cavity to function as an artificial tooth.

Here, since the abutment connects the artificial tooth root and the artificial crown to hold them, it requires a certain degree or more of strength, durability, and compatibility to a biological body. From this viewpoint, titanium alloys are often used as a material to make the abutment. However, since titanium alloys have colors similar to black, when the end portion of the abutment is capped by the artificial tooth crown, black color of the abutment is seen through the artificial tooth crown and sometimes the appearance is not favorable.

With respect to this matter, for example Patent Document 1 (Japanese Patent Application Laid-Open (JP-A) No. 2010-046153) discloses a technique using a ceramic such as zirconia as a material to make an abutment. According to this, it is considered that problems about appearance as mentioned above can be resolved by using a white ceramic.

SUMMARY OF THE INVENTION

Problems to be Solved by the Invention

However, the abutment made of ceramic as mentioned above has problems that the abutment has low toughness by its nature and thus it is easy to be broken. Also, with regard to the color of the abutment, improvement in appearance is desired by making the color even closer to the color of a natural tooth. Further, not only the abutment but also the artificial tooth root has same problems since a part of the artificial tooth root can be visually observed.

Accordingly, an object of the present invention is to provide a dental prosthesis component which is a member for configuring a dental prosthesis provided with an artificial tooth root having a high strength and a good appearance.

Means for Solving the Problems

The present invention will be described below. In order to make the present invention easy to understand, reference numerals given in the accompanying drawings are shown here in parentheses. However, the present invention is not limited to this.

The present invention solves the above problems by a dental prosthesis component (12), (13) which is a member for configuring a dental prosthesis (10) provided with an artificial tooth root (12), wherein the dental prosthesis component is made of Zr-14Nb alloy, a surface layer containing $ZrO_2$ as a main constituent and having a thickness of less than 80 μm is formed on the dental prosthesis component, and a surface of the surface layer has a brightness of Gy 8.0 or more of the color sheets according to Practical Color Co-ordinate System 201. Here, in respect to the brightness, "Practical Color Coordinate System 201" corresponds to the Munsell color system which is an international standard of brightness.

The thickness of the surface layer of the dental prosthesis component is preferably 20 μm or more and less than 80 μm.

Also, a method for producing the above-described dental prosthesis component (12), (13) which is a member for configuring a dental prosthesis (10) provided with an artificial tooth root (12) includes a step of oxidation treatment carried out to a member to be the dental prosthesis component made of Zr-14Nb alloy. In the step, the oxidation treatment is preferably carried out in an atmosphere of 4% or more and 20% or less of oxygen density and in any one of following conditions of (1) to (3).

(1) at 700° C. or more and less than 800° C. for 10 hours
(2) at 800° C. or more and less than 850° C. for 1 hour or more and less than 2 hours
(3) at 850° C. or more and less than 900° C. for 0.5 hours or more and less than 2 hours

Effects of the Invention

According to the present invention, it is possible to provide a dental prosthesis component which is a member for configuring a dental prosthesis provided with an artificial tooth root having a high strength and a good appearance.

MODES FOR CARRYING OUT THE INVENTION

Figure 1:
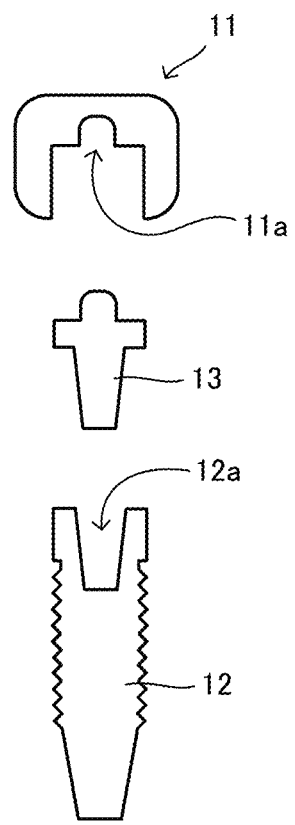
FIG. 1 is a view illustrating a configuration of the dental prosthesis 10.

The functions and benefits of the present invention described above will be apparent from the following aspects for carrying out the invention. Hereinafter, the present invention will be described based on the aspects shown in the drawings. However, the invention is not limited to these aspects.

FIG. 1 is an exploded view schematically showing a configuration of the dental prosthesis 10 illustrating one aspect. The dental prosthesis 10 includes an artificial tooth crown 11, an artificial tooth root 12, and an abutment 13.

The artificial tooth crown 11 is a portion which actually compensates for a defective site in a tooth row. Therefore, the artificial tooth crown 11 has a shape modeled after a natural tooth in appearance, thereby reproducing a shape and texture of the natural tooth. The artificial tooth crown 11 is formed in a container shape and configured in a manner to insert the abutment 13 described below thereinside and connect with the abutment at a receiving portion 11a. As the artificial tooth crown, a known artificial tooth crown may be applied.

The artificial tooth root 12 is included in the dental prosthesis component of the present invention, also called an implant or a fixture, and is a member to be embedded in an alveolar bone so as to adequately fixate the dental prosthesis 10 in an oral cavity. A known form of an artificial tooth root may be applied to the artificial tooth root 12.

The abutment 13 is also included in the dental prosthesis component of the present invention, a member to be disposed between the artificial tooth crown 11 and the artificial tooth root 12 and connect these to hold the artificial tooth crown 11. More specifically, one end of the abutment 13 is fixated in a manner to be inserted into a hole 12a formed to the artificial tooth root 12, and the other end of the abutment 13 is fixated in a manner to be inserted into the artificial tooth crown 11 and be fitted in the receiving portion 11a. A known form of an abutment may be applied to the abutment 13.

Various configurations of a connecting structure of an artificial tooth root and an abutment have been suggested. For example, there is a configuration in which a male screw is formed to an abutment and a female screw is formed to a hole of an artificial tooth root to fixate the abutment and the artificial tooth root by screwing the screws together, or a configuration in which an abutment and an artificial tooth root are fixated by means of different screws. The configurations mentioned above may be applied to the present invention without particular limitations.

The artificial tooth root 12 and/or the abutment 13 as the dental prosthesis component are formed of Zr-14Nb alloy, and their surfaces have a surface layer containing $ZrO_2$ as a main constituent and having a thickness of less than 80 μm. Here, the "main constituent" refers to the constituent accounting for 50% or more of the total constituent of this layer. Measurement of the thickness of the layer may be carried out by a known method without particular limitations. Since the thickness of the surface layer is substantially even, the thickness of the surface layer may be measured by taking photographs of some part of the surface layer by SEM and the like for example. According to this, cracking in the surface layer can be prevented. Here, "no cracking" means that it can be observed there is no cracking occurred in the SEM image at 1000 fold magnification of the cross section of the surface layer. Also, the thickness of the surface layer is preferably 20 μm or more. This makes it possible to adequately secure the thickness of the surface layer whereby it is possible to prevent even certainly the surface of the dental prosthesis component from becoming parti-colored.

Also, the dental prosthesis component is made to have the same or a similar color as that of the artificial tooth crown by having the surface layer. That is, white or a color similar to white. Preferably, the color of the surface of the surface layer is white which has a brightness of Gy 8.0 or more of the color sheets according to Practical Color Co-ordinate System 201.

According to the dental prosthesis component as described above, an improved toughness (that is, strength) can be obtained, and the color becomes closer to the color of a natural tooth. This makes it possible to provide a dental prosthesis component which is a member for configuring a dental prosthesis having an excellent durability with a good appearance, which can endure a long-time usage.

Next, a method for producing the dental prosthesis component according to one aspect will be described. The method for producing the dental prosthesis component includes: a preparing step of a button-shaped ingot made of Zr-14Nb alloy; a molding-cutting step; a processing step; and an oxidation treatment step.

The preparing step of the button-shaped ingot made of Zr-14Nb alloy (hereinafter, the step is sometimes referred to as "step S1") is a step of melting a high-purity Zr (having a purity of 99.6% by mass for example) and a high-purity Nb (having a purity of 99.9% by mass for example) in a proportion with which Zr-14Nb can be formed, and solidifying the resultant. A known method may be applied to this step, and the melting and solidification may be repeated more than once in order to improve the homogeneity.

The molding-cutting step (hereinafter sometimes referred to as "step S2") is a step of melting the ingot obtained in the step S1, obtaining Zr-14Nb in a rod shape by molding, and cutting the rod in a predetermined size. The predetermined size is a size as a starting material which can be applied to a cutting machine in the processing step described below.

The processing step (hereinafter sometimes referred to as "step S3") is a step of disposing the starting material obtained in the step S2 to a processing machine and cutting it to form a shape of the dental prosthesis component. An NC machine tool can be applied for cutting the material as an example, based on a dental CAD/CAM system. Also, polishing may be carried out after the cutting.

The oxidation treatment step (hereinafter sometimes referred to as "step S4") is a step of forming the surface layer described above containing $ZrO_2$ as a main constituent by carrying out oxidation treatment to the resultant member having the shape of the dental prosthesis component obtained by the step S3. Conditions to form the surface layer are as below. Under the air atmosphere (that is, under an oxygen density of about 20%), the material is exposed to a condition satisfying any one of the following conditions of (1) to (3) of treatment temperature and treatment time:

(1) at 700° C. or more and less than 800° C. for 10 hours (2) at 800° C. or more and less than 850° C. for 1 hour or more and less than 2 hours (3) at 850° C. or more and less than 900° C. for 30 minutes or more and less than 2 hours By satisfying the above conditions, the surface layer as described above can be obtained. The oxygen density does not necessarily need to be 20%, but preferably 4% or more and 20% or less, and the oxidation treatment may be carried out in an atmosphere with an oxygen density within the above range.

EXAMPLES

In examples, the treatment temperature and the treatment time in the oxidation treatment step described above were changed, and the $ZrO_2$ layer formed in each case was examined. The treatments were carried out under the air atmosphere. Therefore, the oxidation density was approximately 20%. Samples were disk-shaped Zr-14Nbs each having a diameter of 10 mm. The conditions and the results are shown in Table 1. Here, "time (h)" is a holding time after reaching the treatment temperature (aimed temperature).

In the results, "Thickness" was measured from a photograph of a cross section of the surface layer by SEM, and "○" was given if the thickness of the surface layer was less than 80 μm, and "X" was given if the thickness of the surface layer was 80 μm or more. This is because, as described below, when the surface layer has a thickness of 80 μm or more, cracks increase in the surface layer, which increases a possibility of raising a problem in strength.

"Crack" is the result of evaluation according to degrees of the cracks in the surface layer. In the image of 1000 fold magnification of the surface layer by SEM, "○" was given if a crack was not found, and "X" was given if a crack was found.

"Color" is the evaluation of the surface colors of the samples, and "○" was given if the color had a brightness of Gy 8.0 or more of the color sheets according to Practical Color Co-ordinate System 201, and "X" was given if the color had a brightness below Gy 8.0.

TABLE 1

| | Conditions | | Results (ZrO₂ layer) | | |
|---|---|---|---|---|---|
| No | Temperature (° C.) | Time (h) | Thickness | Crack | Color |
| 1 | 600 | 0.5 | ○ | ○ | X |
| 2 | 600 | 10 | ○ | ○ | X |
| 3 | 700 | 0.5 | ○ | ○ | X |
| 4 | 700 | 10 | ○ | ○ | ○ |
| 5 | 800 | 0.5 | ○ | ○ | X |
| 6 | 800 | 1 | ○ | ○ | ○ |
| 7 | 800 | 2 | X | X | ○ |
| 8 | 800 | 3 | X | X | ○ |
| 9 | 850 | 0.5 | ○ | ○ | ○ |
| 10 | 850 | 1 | ○ | ○ | ○ |
| 11 | 850 | 2 | X | X | ○ |
| 12 | 900 | 0.5 | X | X | ○ |
| 13 | 900 | 1 | X | X | ○ |
| 14 | 1000 | 0.5 | X | X | ○ |

As shown in Table 1, in each of No. 1 to No. 6, No. 9, and No. 10, the thickness of the surface layer (ZrO₂ layer) was less than 80 μm and a crack was not created. Further, in each of No. 4, No. 6, No. 9, and No. 10, it is possible to obtain a dental prosthesis component including a surface layer which is especially excelled in strength and appearance with a desirable color.

On the other hand, No. 1 to No. 3 and No. 5 had a problem of color. The thickness of the surface layer was less than 20 μm each.

In each of No. 11 to No. 14, although the color was desirable, the thickness was 80 μm or more, as a result cracks were created in the surface layer and there was a problem of toughness (strength).

Figure 2A:
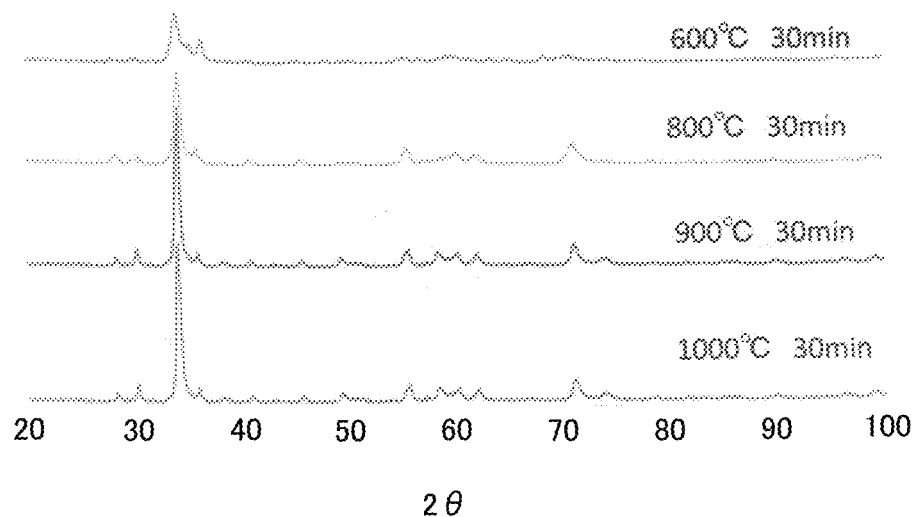
FIG. 2(a) is a graph showing an analysis of X-ray diffraction of surface layers.
Figure 2B:
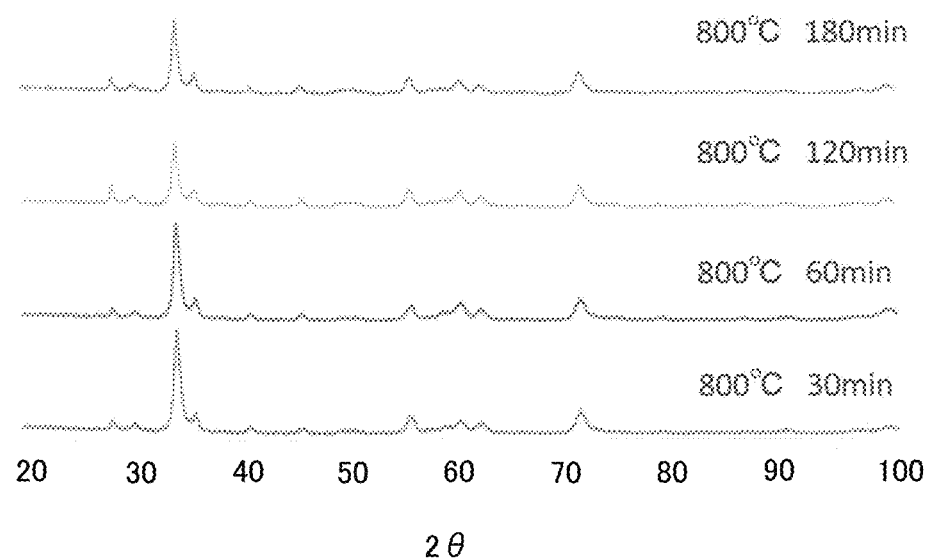
FIG. 2(b) is another graph showing an analysis of X-ray diffraction of the surface layers.

The above results will be described with examples below.
<Constituents of the Surface Layer>
The constituents of the surface layers were examined. The results are shown in FIG. 2(a) and FIG. 2(b). In both of FIG. 2(a) and FIG. 2(b), the horizontal axis represents 2θ, and the vertical axis represents strength. Treatment temperature and treatment time are shown with each line.

Figure 3A:
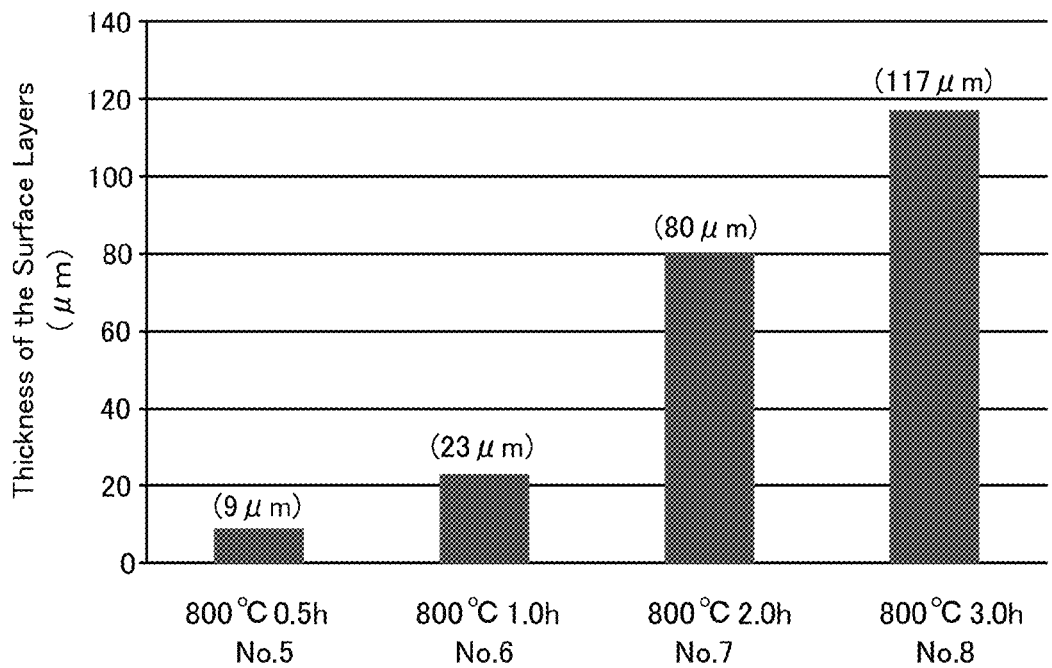
FIG. 3(a) is a graph showing measurement results of thicknesses of the surface layers.
Figure 3B:
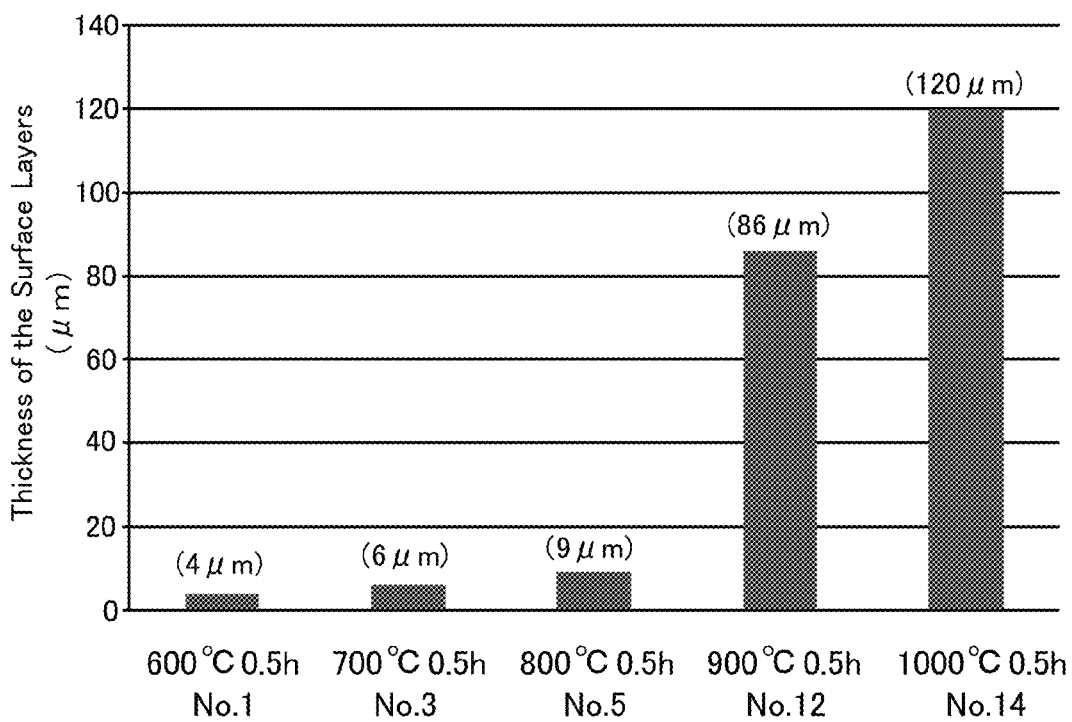
FIG. 3(b) is another graph showing measurement results of thicknesses of the surface layers.

As seen from FIG. 2(a) and FIG. 2(b), it is considered that ZrO₂ monoclinic is most contained in each case. And a slight amount of ZrO₂ in other crystal structure was also contained. On the other hand, NbO and Nbo₂ were hardly detected.
<Thickness of the Surface Layer>
The thickness of the surface layers were examined based on the photographs of cross sections of the surface layers by SEM. FIG. 3(a) is a graph of the examples with the treatment temperature of 800° C. in which the treatment time was changed. FIG. 3(b) is a graph of the examples with the treatment time of 0.5 h in which the treatment temperature was changed. The horizontal axis of each graph represents conditions and the numbers corresponding to Table 1, and the vertical axis represents the thickness of the surface layers.

Figure 4A:
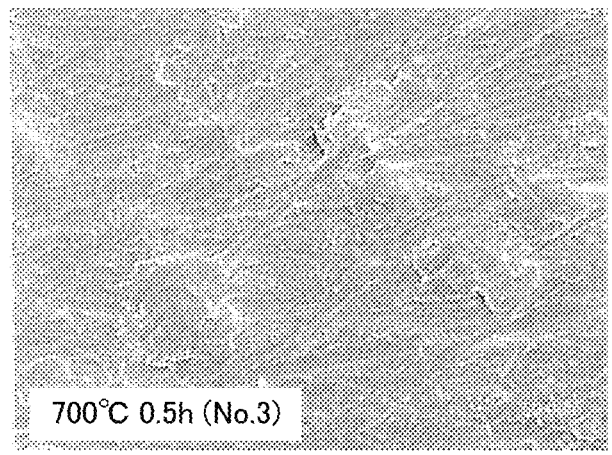
FIG. 4(a) is a photograph of the surface of the surface layer of No. 3.
Figure 4B:
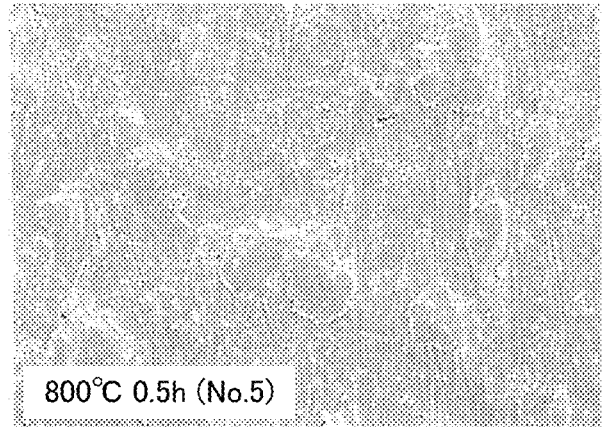
FIG. 4(b) is a photograph of the surface of the surface layer of No. 5.
Figure 4C:
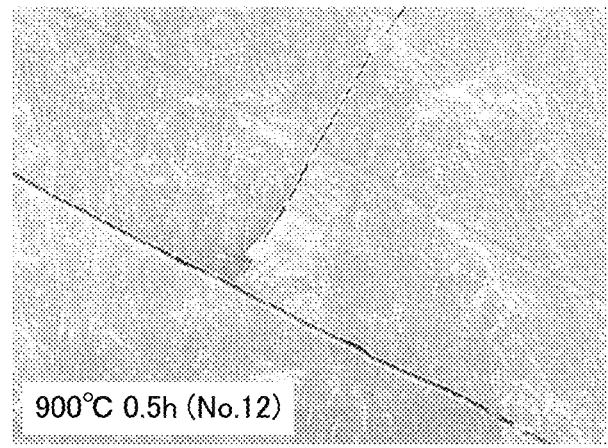
FIG. 4(c) is a photograph of the surface of the surface layer of No. 12.
Figure 5A:
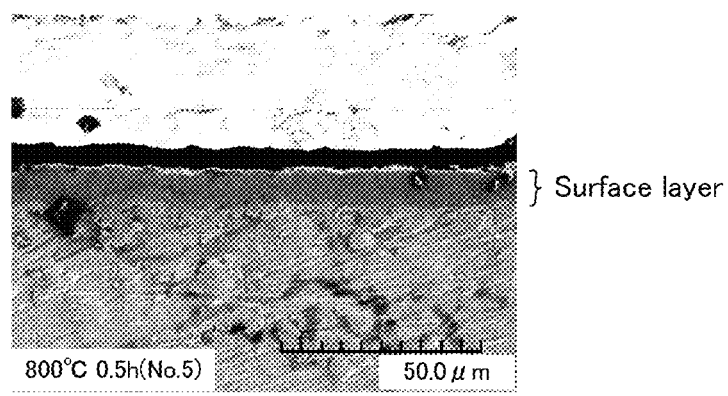
FIG. 5(a) is a photograph of a cross section of the surface layer of No. 5.
Figure 5B:
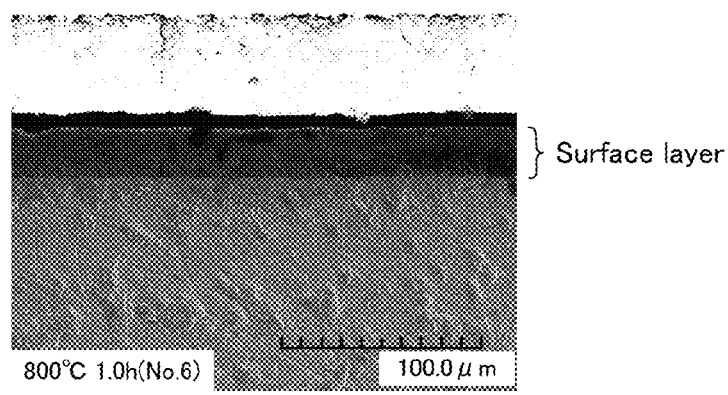
FIG. 5(b) is a photograph of a cross section of the surface layer of No. 6.
Figure 5C:
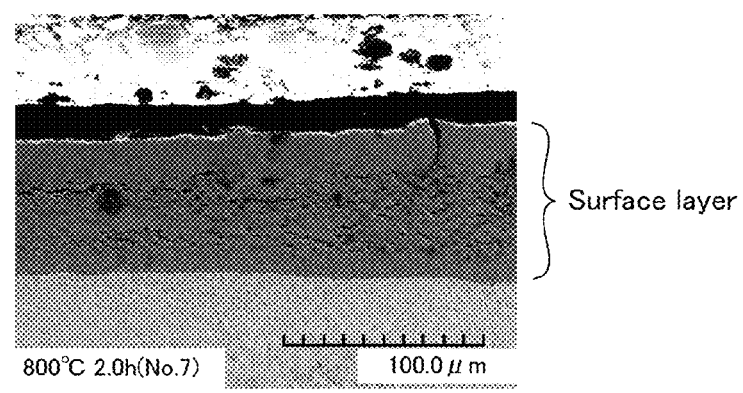
FIG. 5(c) is a photograph of a cross section of the surface layer of No. 7.
Figure 5D:
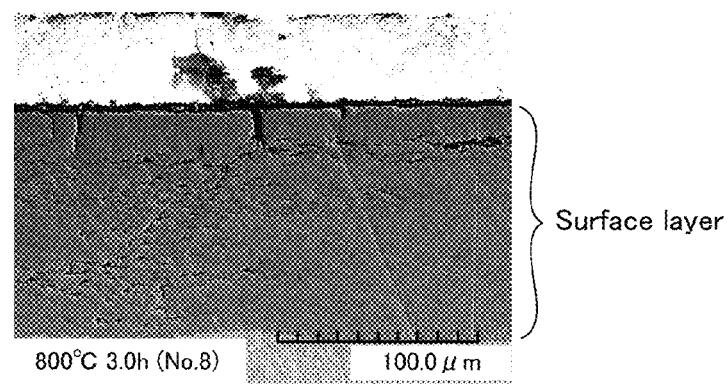
FIG. 5(d) is a photograph of a cross section of the surface layer of No. 8.
Figure 6A:
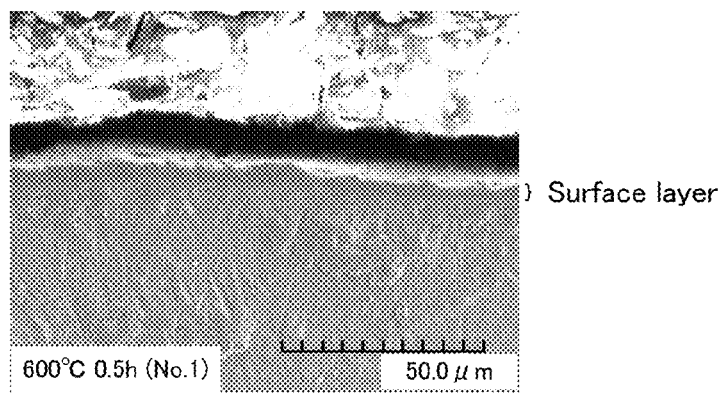
FIG. 6(a) is a photograph of a cross section of the surface layer of No. 1.
Figure 6B:
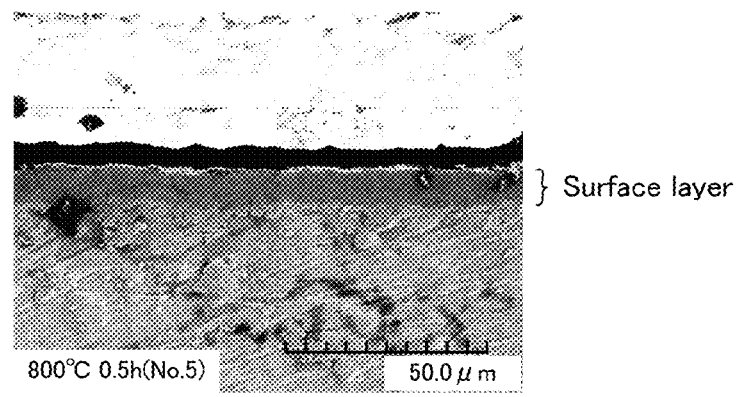
FIG. 6(b) is a photograph of a cross section of the surface layer of No. 5.
Figure 6C:
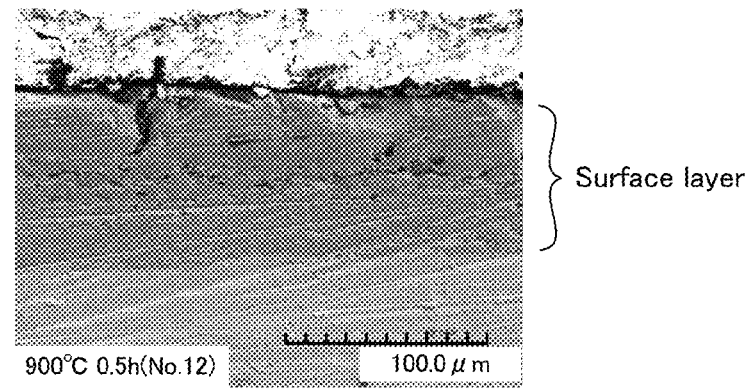
FIG. 6(c) is a photograph of a cross section of the surface layer of No. 12.
Figure 6D:
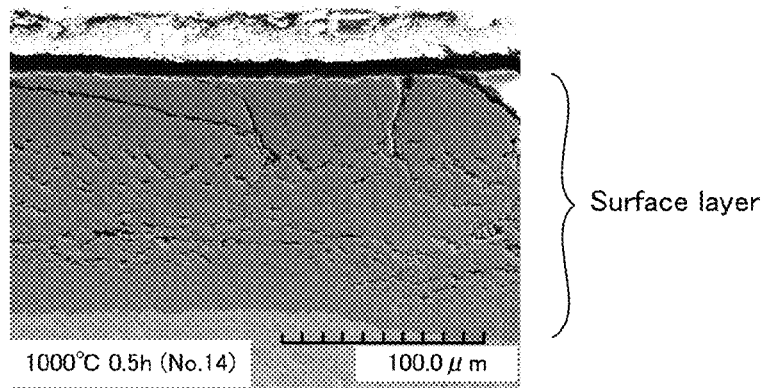
FIG. 6(d) is a photograph of a cross section of the surface layer of No. 14.

As seen from FIG. 3(a) and FIG. 3(b), there is a tendency that the higher temperature and the longer treatment time make the thicker surface layers, and No. 7, No. 8, No. 12, and No. 14 have thicknesses of 80 μm or more.
<Cracks in the Surface Layer>
The cracks created in the surface layers were observed by SEM. FIG. 4(a), FIG. 4(b), and FIG. 4(c) show images of the surface layers by SEM taken from the surface (at 1000 fold magnification). Treatment conditions and numbers corresponding to Table 1 are shown to each figure. As seen from the figures, no cracks were created in No. 3 and No. 5, but cracks were created in the surface layer of example No. 12.

Also, in FIG. 5 and FIG. 6, the images of the cross-sectional surfaces of the surface layers taken by SEM are shown. FIG. 5(a) to FIG. 5(d) are examples in which the treatment temperature was 800° C. and each treatment time was changed. FIG. 6(a) to FIG. 6(d) are examples in which the treatment time was 0.5 h and each treatment temperature was changed. Each of the treatment conditions and the numbers corresponding to Table 1 are shown in each figure.

Figure 7:
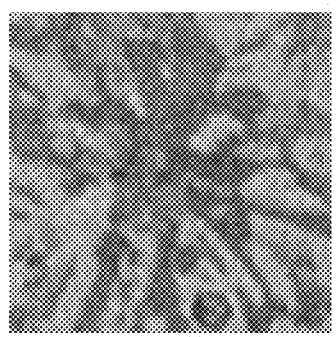
FIG. 7 is a view showing surface colors of samples made under each condition.
Figure 7:
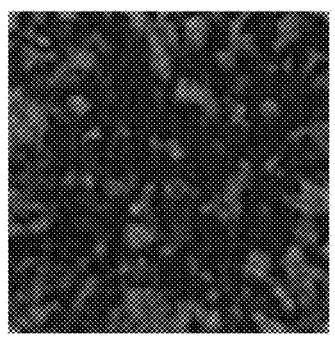
Figure 7:
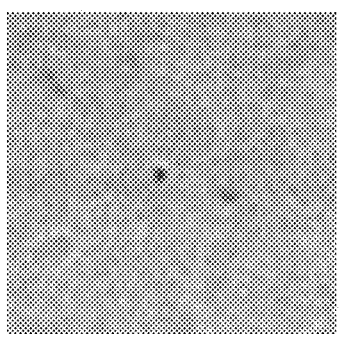
Figure 7:
Figure 7:
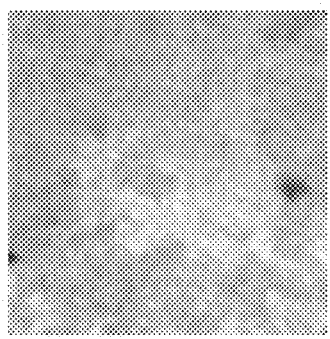
Figure 7:
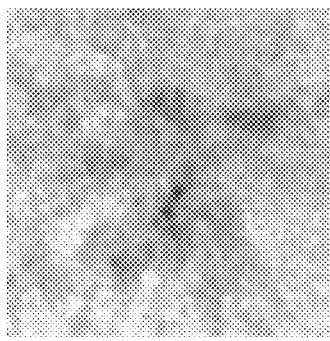
Figure 7:
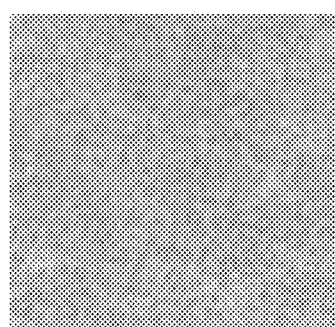
Figure 7:
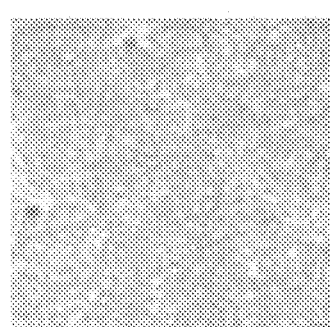

As seen from these figures, cracks were created if the thickness of the surface layer was 80 μm or more (No. 7, No. 8, No. 12 and No. 14).
<Color>
In FIG. 7, examples were shown in which the surface colors of the samples were compared. Each of the treatment conditions and the numbers corresponding to Table 1 were shown with each example. As seen from FIG. 7, in view of the treatment time and the treatment temperature, it is found that a mottling shows up on the surface in a case where the surface layer is thin. Therefore, the mottling is sometimes noticeable depending on the conditions such as size, shape and the like of the samples.

DESCRIPTION OF THE REFERENCE NUMERALS 10 dental prosthesis
11 artificial tooth crown
12 artificial tooth root (dental prosthesis component)
13 abutment (dental prosthesis component)

The invention claimed is:
1. A dental prosthesis, comprising:
an artificial tooth crown;
an artificial tooth root; and
an abutment,
wherein at least one of the artificial tooth crown, the artificial tooth root and the abutment is made of Zr-14Nb alloy, comprises a surface layer containing ZrO₂ and having a thickness between 20 μm and 80 μm formed on at least one of the artificial tooth crown, the artificial tooth root and the abutment, and
the surface of the surface layer has a brightness of Gy 8.0 or more of the color sheets according to Practical Color Co-ordinate System 201.
2. A method for producing a dental prosthesis, the method comprising the step of oxidation treatment carried out on at least one of an artificial tooth crown, an artificial tooth root and an abutment which is made of Zr-14Nb alloy comprising a surface layer containing ZrO₂ and having a thickness between 20 μm and 80 μm formed on at least one of the artificial tooth crown, the artificial tooth root and the abutment, wherein the oxidation treatment is carried out in an atmosphere of between 4% and 20% of an oxygen density and between 700° C. and 800° C. for 10 hours; and wherein the surface of the surface layer of at least one of the artificial tooth crown, the artificial tooth root and the abutment has a brightness of Gy 8.0 or more of the color sheets according to Practical Color Co-ordinate System 201.

3. A method for producing a dental prosthesis, the method comprising the step of oxidation treatment carried out on at least one of an artificial tooth crown, an artificial tooth root and an abutment which is made of Zr-14Nb alloy comprising a surface layer containing $ZrO_2$ and having a thickness between 20 μm and 80 μm formed on at least one of the artificial tooth crown, the artificial tooth root and the abutment, wherein the oxidation treatment is carried out in an atmosphere of between 4% and 20% of an oxygen density and between 800° C. and 850° C., for between 1 and 2 hours; and wherein the surface of the surface layer of at least one of the artificial tooth crown, the artificial tooth root and the abutment has a brightness of Gy 8.0 or more of the color sheets according to Practical Color Co-ordinate System 201.

4. A method for producing a dental prosthesis, the method comprising the step of oxidation treatment carried out on at least one of an artificial tooth crown, an artificial tooth root and an abutment which is made of Zr-14Nb alloy comprising a surface layer containing $ZrO_2$ and having a thickness between 20 μm and 80 μm formed on at least one of the artificial tooth crown, the artificial tooth root and the abutment, wherein the oxidation treatment is carried out in an atmosphere of between 4% and 20% of an oxygen density and between 850° C. and 900° C. for between 0.5 and 2 hours; and wherein the surface of the surface layer of at least one of the artificial tooth crown, the artificial tooth root and the abutment has a brightness of Gy 8.0 or more of the color sheets according to Practical Color Co-ordinate System 201.

* * * * *